United States Patent [19]

Collins, Jr.

[11] Patent Number: 4,802,849
[45] Date of Patent: Feb. 7, 1989

[54] RAPID MANDIBULAR ADVANCEMENT AND VERTICAL AND LATERAL DEVELOPMENT DEVICE

[76] Inventor: John A. Collins, Jr., 1116 Mishawaka Ave., South Bend, Ind. 46615

[21] Appl. No.: 126,026

[22] Filed: Nov. 27, 1987

[51] Int. Cl.⁴ ............................................. A01C 7/00
[52] U.S. Cl. ...................................... 433/19; 433/18; 433/7
[58] Field of Search .................... 433/6, 7, 18, 19

[56] References Cited

U.S. PATENT DOCUMENTS

| | | | |
|---|---|---|---|
| 3,454,001 | 7/1969 | Stakfisch | 433/6 |
| 4,239,487 | 12/1980 | Murdock | 433/7 |
| 4,433,956 | 2/1984 | Witzig | 433/7 |
| 4,571,178 | 2/1986 | Rosenberg | 433/7 |

Primary Examiner—Robert Peshock
Attorney, Agent, or Firm—Thomas J. Dodd

[57] ABSTRACT

A functional orthodontic appliance which includes permanent magnets embedded in the upper and lower acrylic positioning parts normally positioned behind the incisor teeth of the patient. The magnets are of opposite polarity on the top and bottom parts and positioned so as to influence movement of the patient's mandible into a vertical bite plane. The appliance may also include positioning wires and springs for promoting back tooth eruption corresponding to the change in the bite plane, and lateral expansion screws to promote mouth arch expansion.

10 Claims, 3 Drawing Sheets

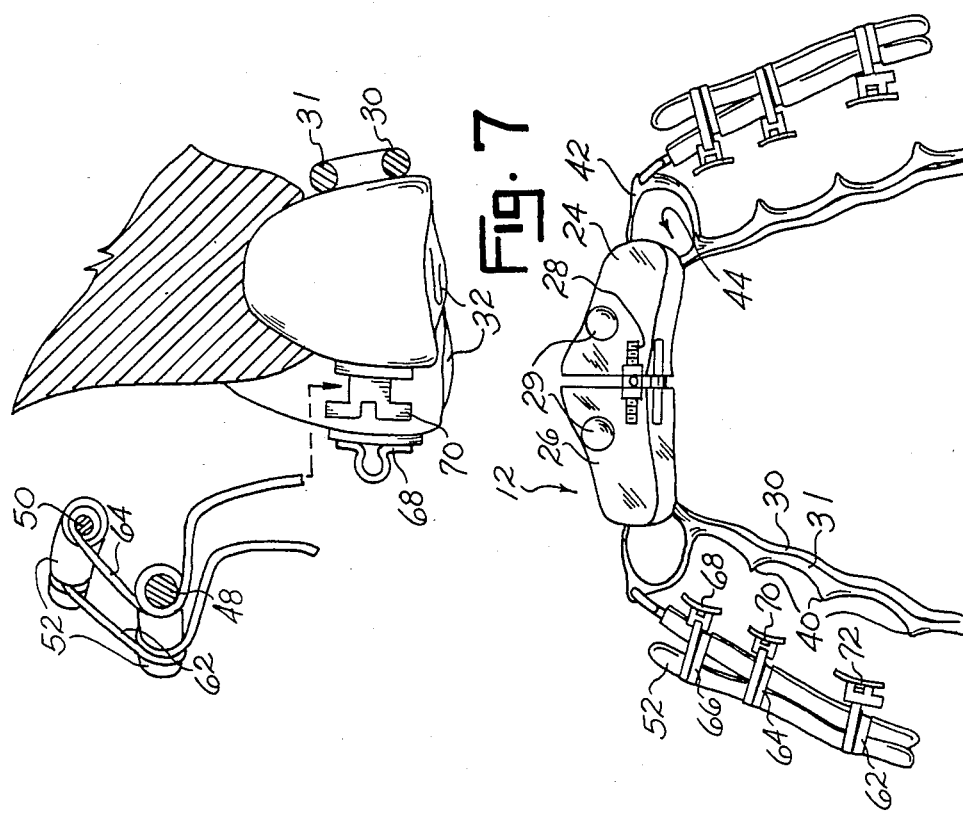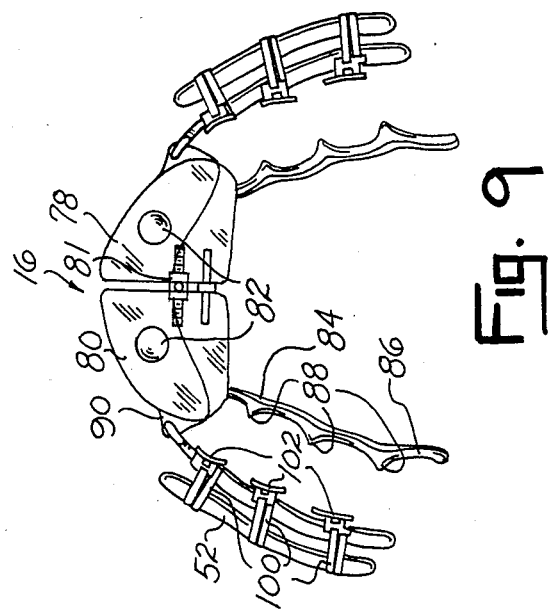

RAPID MANDIBULAR ADVANCEMENT AND VERTICAL AND LATERAL DEVELOPMENT DEVICE

SUMMARY OF THE INVENTION

This invention relates to a functional orthodontic appliance and will have application to an appliance for promoting proper Functional orthodontic appliances have risen to prominence in the past few years among orthodontists as a revolutionary way of correcting flawed cephalometric profiles of patients. Such appliances are popular with patients due to their rapid effectiveness, coupled with comfortable wear and removability. While man orthodontists have praised the rapidity with which these appliances accomplish correction, this correction is often delayed due to patient misuse or nonuse of the appliance according to the doctor's wearing schedule. Some examples of functional appliances are shown in my U.S. Pat. No. Des. 290,502, Des. 290,503, Des. 290,504, and Des. 290,505.

The functional appliance of this invention is a hybrid design which incorporates several features to allow for correction of one or more of a number of cephalometric and tooth position flaws. The appliance is also designed for full-time wearing by the patient, which reduces correction time by removing patient cooperation as a factor. By adding or deleting additional device components, the functional appliance of this invention can correct up to four different problems in the patient's cephalometric profile, while it is more comfortable to wear than other devices which are designed to correct only one such flaw.

Accordingly, it is an object of this invention to provide for a novel functional orthodontic appliance.

Another object of this invention is to provide for a functional appliance which is more comfortable to wear and does not impede speech to the same degree as previous appliances.

Another object of this invention is to provide for a functional appliance which efficiently corrects one or a number of cephalometric and tooth position flaws more rapidly than previous appliances.

Still another object of this invention is to provide for a functional appliance which eliminates patent cooperation as a factor in correction time.

Other objects of this invention will become apparent upon a reading of the following description.

BRIEF DESCRIPTION OF THE DRAWINGS

FIG. 7 is a sectional view similar to FIG. 6 showing removal of the side springs.

FIG. 8 is a plan view of the lower half of the appliance.

FIG. 9 is a plan view of the upper half of the appliance.

DESCRIPTION OF THE PREFERRED EMBODIMENT

Figure 1:
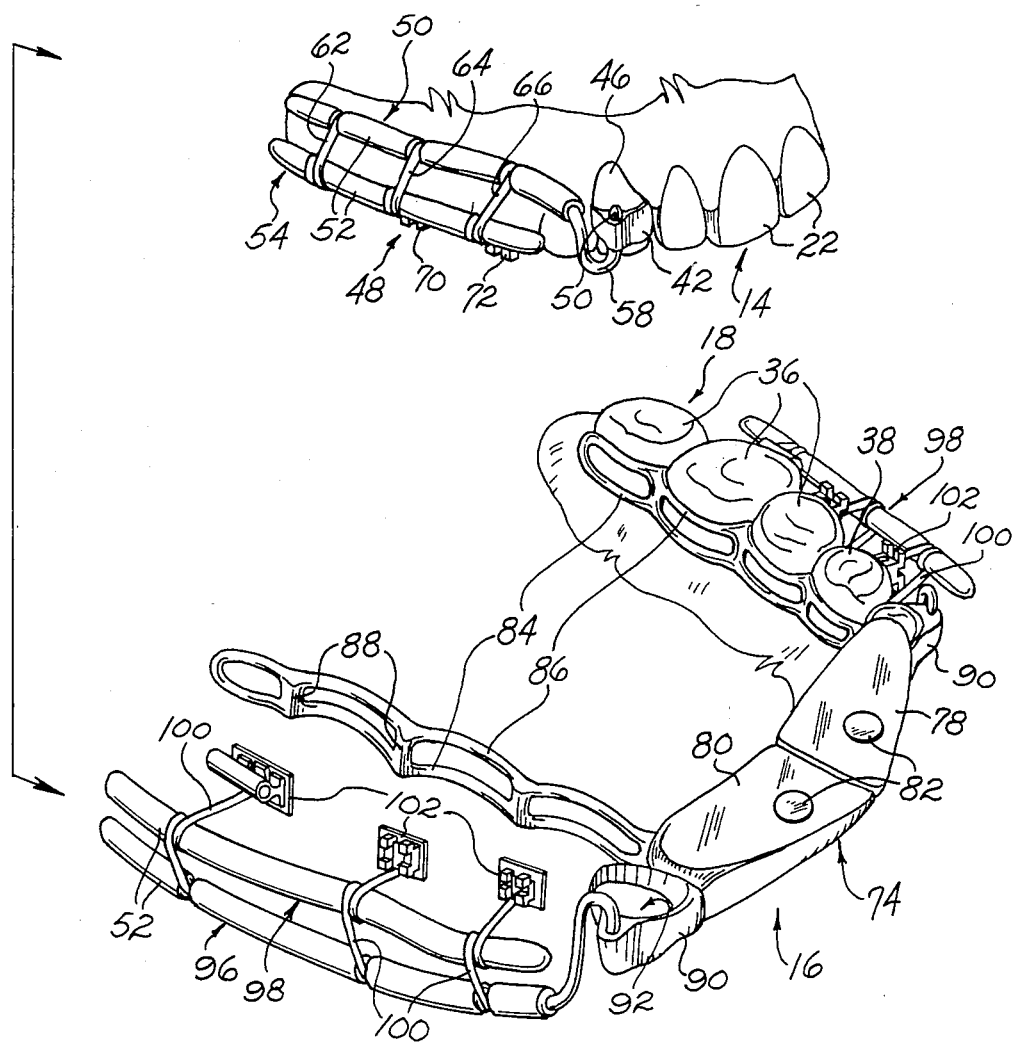
FIG. 1 is an exploded fragmentary perspective view functional appliance of this with some teeth shown to illustrate its use.
Figure 2:
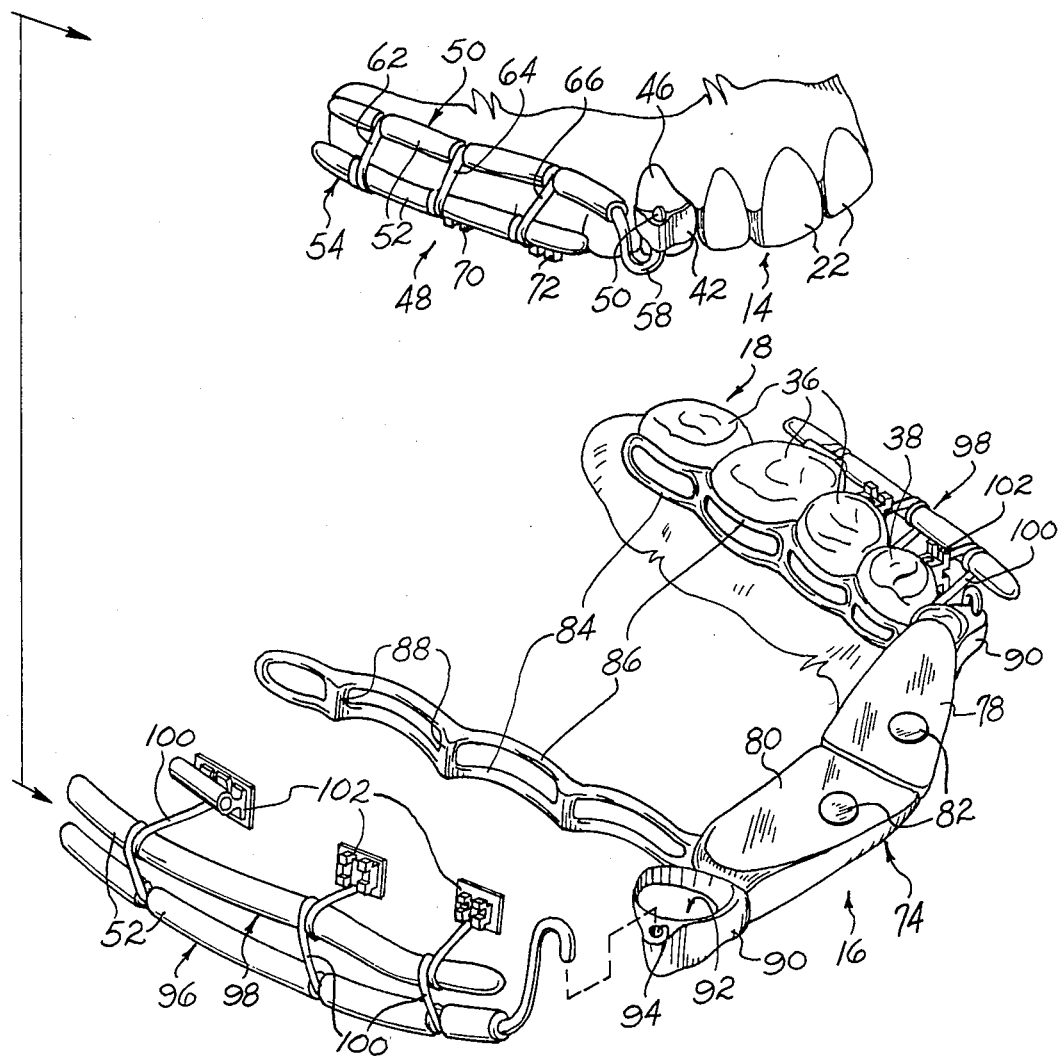
FIG. 2 is an exploded fragmentary perspective view of the appliance showing the removability of the side springs.
Figure 3:
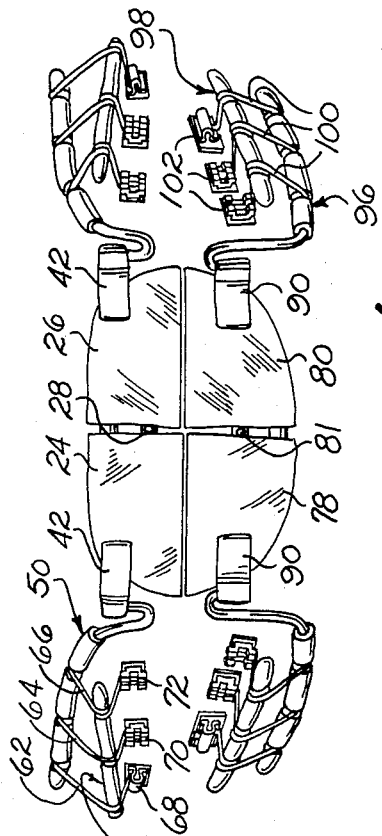
FIG. 3 is a side elevation view of the appliance.
Figure 6:
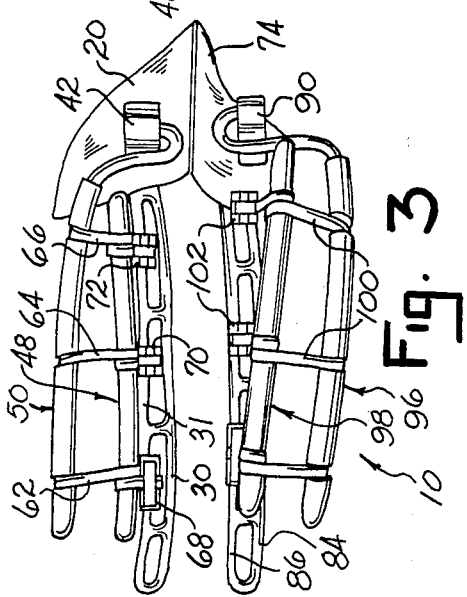
FIG. 6 is a sectional view taken along line 6—6 of FIG. 5.
Figure 4:
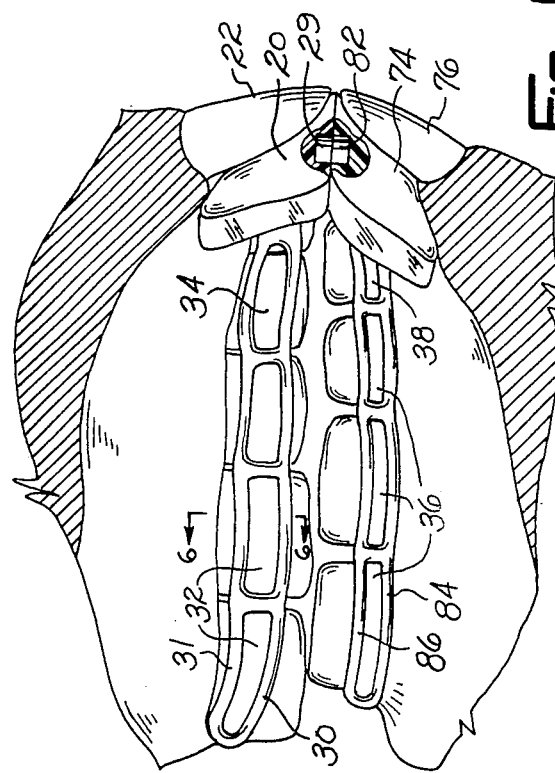
FIG. 4 is a partial front elevation view of the appliance.

The preferred embodiment herein described is not intended to be exhaustive or to limit the invention to the precise forms disclosed. It is chosen and described to explain the principles of the invention and its application and practical use to enable others skilled in the art to utilize the invention.

Referring now to the drawings, reference numeral 10 generally refers to the functional appliance of this invention. Appliance 10 generally includes an upper part 12 adopted for fitting in the upper part of the patient's mouth adjacent the upper teeth 14, and a lower part 16 adapted for fitting in the lower part of the patient's mouth adjacent the lower teeth 18. It is understood that both upper and lower parts 12 and 10 are formed according to the specifications of each individual patient's teeth The teeth 14 and 18 depicted in the drawings are for illustrative purposes only and with the exact configuration of the appliance 10 being adjustable to accommodate nearly all tooth and jaw configurations of a human being.

Figure 5:
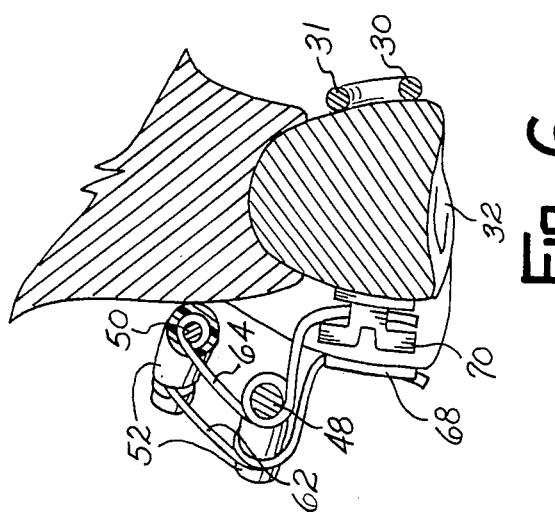
FIG. 5 is a partial sectional view of the appliance shown in use in the mouth.

Upper part 12 as shown in plan view in FIG. 9 includes an acrylic piece 20 which is configured to accurately fit behind the patient's upper incisor teeth 22 as seen in FIG. 5. Acrylic piece 20 is preferably formed of two separate acrylic pieces 24 and 26, as shown, which are joined by an adjustable expansion screw arrangement 28 which is conventional and known in this art field. Positioned in acrylic pieces 24 and 26 and adjacent the outer edge thereof are one or more permanent metal magnets (two shown) 29.

Extending rearwardly of each acrylic piece 24, 26 are rigid metal shaping wires 30, 81 respectively. Each wire 30, 31 is connected to its respective acrylic piece 24, 26 and is formed according to the configuration of the patient's upper molars 82 and bicuspids 84 and to the lower molars 36 and bicuspids 38. Each wire 80, 31 is preferably continuous as shown and includes outwardly extending integral wedges 40 which fit between molars 32, 36 and bicuspids 84, 88 as shown in FIG. 1.

Upper part 12 further includes a flange 42 attached to one or both acrylic pieces 24, 26. Flange 42 defines a central opening 44 which also the flange to be fitted over the patient's upper cuspid 46 to secure upper part 12 to upper teeth 14. Flange 42 further defines a peripheral bore 47 positioned outwardly of teeth 14 when upper part 12 is installed.

One or more expansion bars 48 (two shown) may be positioned along the outer edges of upper teeth 14. Each expansion bar 48 preferably includes an upper bar 50 and a lower bar 54 covered by soft polymeric or rubber cheek shields Each upper bar 50 includes a raised hook part 58 respectively which is fittable removably within peripheral bores 49 or ranges 42. Upper bars 50 are connected to lower bars 54 by active vertical flat springs 62, 64 and 66 which are formed of resilient metal and fixedly connected to each lower bar and are wound about the upper bar as shown. A plurality of attachment lugs (three shown) 68, 70 and 72, are secured to the outside surface of upper teeth 14 as shown. Springs 62-66 are slidably connected to a respective lug 68-72 as shown and serve to exert downward pressure on upper teeth 14 to promote tooth eruption.

Lower part 16 as shown in plan view in FIG. 9 includes acrylic piece 74 (See FIG. 5) which is configured to accurately fit behind the patient's lower incisor teeth 76 as also seen in FIG. 5. Acrylic piece 74, like acrylic piece 20, is preferably formed of two separate pieces 78, 80 joined by a conventional expansion screw 81. Positioned adjacent the outer edge of each piece 78, 80 are metal magnets (two shown) 82 which of opposite (attracting) polarity to and which align with magnets 29 to lock the patient's mandible (not shown) in the preferred arrangement with the leading edges of incisor teeth 22, 76 in the vertical position shown in FIG. 5. Magnets 29, 82 are of sufficient strength to deter lateral or forward or backward shifting during rest, but are also of insufficient strength to prevent the patient from opening his mouth to speak or eat.

Lower part 16 also includes rigid shaping wires 84, 86 similar to upper part wires 80, and wedges 88 similar to wedges 40 Lower part 16 may further include flanges 90 which define bores 92 and 94 similar to their upper part 12 counterparts and expansion bars 96, 98 which with their active springs 100 and lugs 102 perform the same function (active eruption) on the lower teeth 18 as their counterparts do on the upper teeth 14.

Each functional appliance 10 is constructed as per the patient's individual needs noted by a private orthod positioning of magnets 29, 82 in acrylic pieces 24, 26, 78, and 80 is determined by the desired position and length of travel of the patient's mandible necessary to achieve the ideal bite plane shown in FIG. 5. The orthodontist will also recommend the use or absence of active springs 62–66 and 100 depending on whether active or passive eruption of the molars and/or bicuspids is desired. After construction of the appliance 10, the individual orthodontist will install the device in the patient's mouth. If lateral expansion of one or both of the patient's mouth arches is desired, expansion screws 28 and/or 82 will be turned to laterally move individual acrylic pieces 30, 31 and/or 78, 80, which also tends to drive wedges 40 and/or 88 between the molars and bicuspids to promote tooth eruption. Flanges 42 and 90 will normally then be secured about the patient's cuspid teeth to prevent removal of appliance 10 by the patient. Appliance 10 may then be periodically adjusted by the orthodontist until treatment is finished, usually 3 to 9 months later, when the orthodontist removes the appliance.

The above-described embodiment does not limit this invention to the scope of the details given, but may be modified and expanded within the scope of the following claims.

I claim:

1. A functional appliance adapted to be worn in the mouth of a patient adjacent upper and lower rows of teeth, said appliance comprising an upper part for wearing in an upper part of the mouth adjacent the upper teeth and arch, and a lower part for wearing in a lower part of the mouth adjacent the lower teeth and arch, each upper part and lower part including a rigid tooth positioning part located in abutment behind upper and lower incisor teeth in said patient's mouth, flexible metal positioning wires extending rearwardly of each positioning part located adjacent upper and lower molars in said patient's mouth, each positioning part including magnet means for, mating the positioning parts to position said incisor teeth in a substantially vertical bite plane which promotes movement of said mandible into an ideal bite position.

2. The functional appliance of claim 1 wherein said positioning wires are located adjacent an inner side of said molars, said positioning wires including a plurality of wedges extending between said molars and constituting means for separating said teeth to promote eruption of the molars.

3. The functional appliance of claim 1 wherein said acrylic positioning part includes first and second acrylic pieces joined by an expansion screw, said expansion screw constituting means for adjusting the space between said first and second acrylic positioning parts to promote lateral expansion of said upper and lower arches.

4. The functional appliance of claim 8 wherein said acrylic positioning part includes first and second acrylic pieces joined by an expansion screw, said expansion screw constituting means for adjusting the space between said first and second acrylic positioning parts to promote lateral expansion of said upper and lower arches.

5. The functional appliance of claim 1 wherein each positioning part includes a bar extending laterally of each positioning part adjacent an outer surface of said molars, lug means connected to said molar outer surface indirectly connecting said bar to said molars, and spring means connected between said bar and said lug means for urging said upper and lower molars towards each other.

6. The functional appliance of claim 5 wherein said bar includes first and second vertically speed bar members, one of said first and second bar members detachably connected to said positioning part, said spring means including a flexible metal spring having a first terminal end connected to said first bar member, said spring wrapped about said second bar member and including a second terminal end detachably connected to a said lug means wherein expansion forces exerted by said spring are transferred to said molars.

7. The functional appliance of claim 5 wherein said upper and lower parts each include clamp means for firmly fastening said appliance to said patient's upper and lower teeth wherein manual removal by the patient is prevented.

8. The functional appliance of claim 7 wherein said clamp means includes a flange connected to each positioning part, said flange defining an opening through which is fitted restrictively one of said patient's teeth.

9. The functional appliance of claim 8 wherein said flange further defines a bore, said eruption means including a hook part removably fitted within said base.

10. The functional appliance of claim 6 and soft protective means overlying each bar member for preventing sharp contact with flexible tissues within the patient's mouth.

* * * * *